United States Patent
Yanagisawa et al.

(10) Patent No.: US 7,569,388 B2
(45) Date of Patent: Aug. 4, 2009

(54) PLANTS HAVING AN ENHANCED AMINO ACID CONTENT, PLANTS HAVING AN ENHANCED NITROGEN CONTENT, PLANTS TOLERANT TO NITROGEN DEFICIENCY, AND METHODS FOR PRODUCING THEM

(75) Inventors: Shuichi Yanagisawa, Tokyo (JP); Tetsuya Miwa, Kawasaki (JP); Ai Akiyama, Kawasaki (JP); Hiroaki Kisaka, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 464 days.

(21) Appl. No.: 10/360,634

(22) Filed: Feb. 10, 2003

(65) Prior Publication Data

US 2003/0177520 A1 Sep. 18, 2003

(30) Foreign Application Priority Data

Feb. 19, 2002 (JP) .............................. 2002-040947
Jul. 24, 2002 (JP) .............................. 2002-214783

(51) Int. Cl.
*A01H 1/00* (2006.01)
*C07H 21/04* (2006.01)
*C07K 14/415* (2006.01)
*C12N 15/00* (2006.01)

(52) U.S. Cl. .......................... 435/419; 435/6; 435/69.1; 435/468; 435/320.1; 530/370; 536/23.6; 800/278; 800/295

(58) Field of Classification Search ....................... None
See application file for complete search history.

(56) References Cited

U.S. PATENT DOCUMENTS

2002/0040489 A1* 4/2002 Gorlach et al. .............. 800/288

OTHER PUBLICATIONS

Yanagisawa (Trends in Plant Science, 7:555-560, 2002).*
Yanagisawa (Plant Journal, 213:281-288, 2000).*
Yanagisawa et al. (Plant Cell 10: 75-89, 1998).*
Yanagisawa et al. (NCBI, GenBank, Sequence Accession No. X66076, pp. 1-2, published Dec. 8, 1995).*
Valvekens et al. (PNAS, 85:5536-5540, 1998).*
Edwards (Nature Biotechnology, 17:22-23, 1999).*
Remi Vincent, et al. "Overexpression of a Soybean Gene Encoding Cytosolic Glutamine Synthetase in Shoots of Transgenic *Lotus corniculatus* L. Plants Triggers Changes in Ammonium Assimilation and Plant Development," Planta, 201, 1997, pp. 424-433.
Shuichi Yanagisawa, "DOF DNA-Binding Proteins Contain a Novel Zinc Finger Motif," Trends in Plant Science, vol. 1, No. 7, Jul. 1996, p. 213.
Shuichi Yanagisawa, et al. "Involvement of Maize DOF Zinc Finger Proteins in Tissue-Specific and Light-Regulated Gene Expression," The Plant Cell, vol. 10, Jan. 1998, pp. 75-89.
Timothy Brears, et al. "Ectopic Overexpression of Asparagine Synthetase in Transgenic Tobacco," Plant Physiol., vol. 103, pp. 1285-1290.
Hong-Gu Kang, et al. "Characterization of Salicylic Acid-Responsive, *Arabidopsis* DOF Domain Proteins: Overexpression of OBP3 Leads to Growth Defects," The Plant Journal, 21(4), 2000, pp. 329-339.
Shuichi Yanagisawa, "DOF1 and DOF2 Transcription Factors are Associated with Expression of Multiple Genes Involved in Carbon Metabolism in Maize," The Plant Journal, 21(3), 2000, pp. 281-288.
Stitt, M, et al., "Steps Towards an Integrated View of Nitrogen Metabolism," Journal of Experimental Botany, vol. 53, No. 370, Inorganic Nitrogen Assimilation Special Issue, Apr. 2002, pp. 959-970.
Lam, H. M., et al., "The Molecular-Genetics of Nitrogen Assimilation Into Amino Acids In Higher Plants," Annu. Rev. Plant Mol. Biol. 1996, 47, pp. 569-593.
Foyer, C. H., et al., Markers and Signals Associated with Nitrogen Assimilation in Higher Plants,: Journal of Experimental Botany, vol. 54, No. 382, Regulation of Carbon Metabolism Special Issue, Jan. 2003, pp. 585-593.
Thomas Rademacher, et al., "An Engineered Phosphoenolpyruvate Carboxylase Redirects Carbon and Nitrogen Flow in Transgenic Potato Plants", The Plant Journal (2002) 32, pp. 25-39.
Li-Mei Chen, et al., "Overexpression of a Cyanobacterial Phosphoenolpyruvate Carboxylase with Diminished Sensitivity to Feedback Inhibition in *Arabidopsis* Changes Amino Acid Metabolism", Planta (2004) 219, pp. 440-449.
Jeanneau, M., et al., "Manipulating PEPC Levels in Plants," Journal of Experimental Botany, vol. 53, No. 376, Sep. 2002, pp. 1837-1845.
Häuslet, R. E., et al., "Overexpression of $C_4$-Cycle Enzymes in Transgenic $C_3$ Plants: A Biotechnological Approach to Improve $C_3$-Photosynthesis," Journal of Experimental Botany, vol. 53, No. 369, Apr. 2002, pp. 591-607.
Yanagisawa, S., et al., "Metabolic Engineering with Dof1 Transcription Factor in Plants: Improved Nitrogen Assimilation and Growth Under Low-Nitrogen Conditions," PNAS, vol. 101, No. 20, May 18, 2004, pp. 7833-7838.
Rolletschek, H., et al., "Seed-Specific Expression of a Bacterial Phosphoenolpyruvate Carboxylase in *Vicia narbonensis* Increases Protein Content and Improves Carbon Economy," Plant Biotechnology Journal, vol. 2, 2004, pp. 211-219.

* cited by examiner

*Primary Examiner*—Phuong T Bui
(74) *Attorney, Agent, or Firm*—Oblon, Spivak, McClelland, Maier & Neustadt, P.C.

(57) ABSTRACT

The object of the present invention is to provide a transformed plant having an enhanced amino acid content, a progeny of the plant, seeds of the plant and a method for producing the plant. The present invention provides a transformed plant having a gene encoding DNA binding protein of Dof family and also having a free amino acid content higher than that of naturally occurring plants of the same species cultivated under the same conditions. The present invention also provides a method of producing a transformed plant having the free amino acid content higher than that of naturally occurring plants of the same species cultivated under the same conditions by introducing a gene encoding DNA binding protein of Dof family into the plant to express the gene in the plant body.

4 Claims, 4 Drawing Sheets

PLANTS HAVING AN ENHANCED AMINO ACID CONTENT, PLANTS HAVING AN ENHANCED NITROGEN CONTENT, PLANTS TOLERANT TO NITROGEN DEFICIENCY, AND METHODS FOR PRODUCING THEM

BACKGROUND OF THE INVENTION

The present invention relates to a transformed plant having an enhanced free amino acid content, a plant having enhanced nitrogen content, a plant tolerant to nitrogen deficiency, and a method for producing the plant.

Plants are autotrophic, and they are capable of synthesizing all the compounds indispensable for living. Amino acids are included in these compounds. Plants synthesize all of the 20 naturally occurring amino acids from water, carbon dioxide and inorganic nitrogen sources utilizable in the environment by making use of light energy. Animals including human beings cannot synthesize all the amino acids. Amino acids that cannot be synthesized by animals are called "essential amino acid(s)" and the intake of the essential amino acid(s) is nutritionally important. Animals principally depend on the amino acids synthesized by the plants for these essential amino acids. Therefore, it has been considered that the improvement in the quality and amount of amino acids contained in plants is an important issue for increasing the nutritional value of plants.

Further, the increase in the capacity of plants for synthesizing amino acids is also significant from the viewpoint of the growth of the plants themselves. As described above, plants synthesize amino acids from inorganic nitrogen in the environment. For the plants, the process for the synthesis of amino acids is also the process for the assimilation and absorption of nitrogen as amino acids. Namely, plants assimilate nitrogen in its final form as ammonia into glutamic acid, and glutamic acid is distributed and utilized as a nitrogen source of various components, such as other amino acids and nucleic acid, of living bodies. Accordingly, the increase in the capacity of plants for synthesizing amino acids is, in other words, an improvement in nitrogen utilization efficiency of plants. Nitrogen is one of major limiting factors for the growth of plants. If the capacity of nitrogen assimilation may be increased as a result of the increase in the amino acid-synthesizing capacity, the acceleration of the growth of the plants is expected and, accordingly, an increase in the yield thereof is also expected. In addition, if nitrogen may be efficiently used, it would be expected that the amount of inorganic nitrogen used as fertilizers may be minimized and the environmental load may be reduced.

It is considered that one of the methods for increasing an amino acid content of plants is the enhancement of the enzymatic reaction responsible for the above-described nitrogen assimilation. Generally in plants, nitrogen is reduced to form ammonia and then assimilated into glutamic acid by glutamate synthase (GOGAT) and glutamine synthetase (GS). It has been attempted, therefore, to increase an amino acid content and nitrogen content of plants by enhancing enzyme systems concerning the process for the generation and transportation of ammonia, the regulation of GOGAT or GS activity or the transportation and translocation of the assimilated amino acids. The attempts include, for examples, the introduction of soybean GS into Lotus corniculatus (Planta 1997; 201(4): 424-33, Vincent R et al.) and the introduction of asparagine synthase derived from Arabidopsis thaliana into Arabidopsis thaliana (JP-Kokai No. 9-503389, Coruzzi G et al.). However, in such examples, a significant increase in the absolute amino acid content or the absolute nitrogen content was not found, although a change in the relative contents of amino acids was found.

Besides these investigations, an investigation has been made on a DNA binding protein which specifically binds to the promoter domain of C4 type phosphoenol pyruvate carboxylase (PEPC) gene concerning the carbon dioxide assimilation. As such a DNA binding protein, Dof1 protein and the gene thereof were found in maize (Yanagisawa, S. (1993), Trends in Plant Sci., 1 (7), 213). Dof1 is a DNA binding protein unique to plants which has only one zinc(Zn)-finger-like domain. During the investigations, using a transient expression system of maize mesophyll protoplast, it was elucidated that Dof1 accelerates the transcription of C4 phosphoenol pyruvate carboxylase (PEPC) gene. It was also elucidated that Dof1 also accelerates the transcription of C3 phosphoenol pyruvate carboxylase gene and cytoplasmic pyruvate ortho-phosphate dikinase (PPDK) gene. It was also shown that a high Dof1 activity is observed in the leaves under the light. The function of the phosphoenol pyruvate carboxylase is to assimilate bicarbonate into phosphoenolpyruvate and to provide TCA cycle with oxaloacetate, and the function of the cytoplasmic pyruvate ortho-phosphate dikinase is to generate phosphoenolpyruvate from pyruvic acid and to provide the substrate of phosphoenol pyruvate carboxylase.

The DNA binding proteins having only one zinc-finger-like domain, which derive from plants, are called "Dof family". After the search on the genome of Arabidopsis thaliana, 37 proteins belonging to the Dof family were found. Among them, a transformed plant expressing the Dof family binding protein called OBP3 has been produced. However, among those Dof family proteins, a homology is scarcely recognized except for the Zinc-finger portion and, in addition, the functions of them have never been reported except for Dof1. In fact, no phenotypes relevant to OBP3 were reported in the transformed plants to which the above-described OBP3 gene had been introduced. Further, even for Dof1, the function of which has been elucidated to some extent, it is never reported that a transformed plant was produced into which this gene had been introduced, and the physiological function of Dof1 in the plant body has not been sufficiently elucidated. In addition, the amino acid content of the transformed plant having Dof1 gene was not determined.

SUMMARY OF THE INVENTION

The object of the present invention is to provide a transformed plant having an enhanced amino acid content and/or a plant having an enhanced nitrogen content and/or a plant tolerant to nitrogen deficeincy, progenies of the plants, seeds of them and methods for producing them.

The inventors had an idea that the reason why an amino acid content is not enhanced by enhancing the enzymes responsible for the nitrogen assimilation reactions is that the supply of carbon to be utilized for the nitrogen assimilation is insufficient. The inventors focused on the control of a group of enzyme systems responsible for the metabolic pathway leading from triose (dihydroxyacetone phosphate) to 2-oxoglutaric acid, which is an important pathway for supplying carbon. In view of the difficulty of regulating each of numerous enzymes by, for example genetic recombination techniques, the inventors sought a regulatory factor capable of controlling these genes, i.e. the master control gene. As a result, the inventors have found that the object of the present invention can be attained by using a protein belonging to Dof family and the gene encoding it to establish the present invention.

Namely, the present invention relates to a transformed plant to which a gene encoding DNA binding protein belonging to Dof family is introduced and contains a higher content of free amino acid(s) than that of a naturally occurring plant of the same species cultivated under the same conditions, and a seed thereof. The present invention also relates to a plant having increased nitrogen content enhanced by such a metabolic modification and/or a plant tolerant to nitrogen deficiency.

The present invention also relates to a method for producing a transformed plant having a free amino acid content higher than that of a naturally occurring plant of the same species cultivated under the same conditions, comprising introducing a gene encoding a DNA binding protein of Dof family into a plant to express the gene in the plant body. The present invention also relates to a method for producing a plant having an enhanced nitrogen content and/or a transformed plant tolerant to nitrogen deficiency by such a metabolic modification.

In particular, the present invention relates to the above-described transformed plant and a seed thereof, wherein the DNA binding protein belonging to Dof family increases the amount of the transcription of phosphoenol pyruvate carboxylase gene and/or cytoplasmic pyruvate ortho-phosphate dikinase gene.

Further, the present invention relates to the above-described method for producing a transformed plant, wherein the DNA binding protein of Dof family is the protein which increases the amount of the transcription of phosphoenol pyruvate carboxylase gene and/or cytoplasmic pyruvate ortho-phosphate dikinase gene.

In particular, one example of the DNA binding protein of Dof family used in the present invention is maze Dof1 protein.

DESCRIPTION OF THE PREFERRED EMBODIMENTS

Figure 1A:
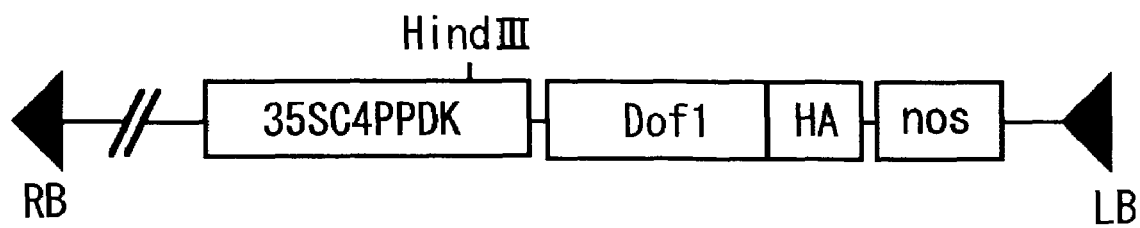
FIG. 1A is a schematic view showing the Dof1-inserted region in the plasmid pBI121 Dof1.

In the present invention, a plant having an enhanced amino acid content and/or a plant having an enhanced nitrogen content and/or a plant tolerant to nitrogen deficiency can be obtained by introducing a nucleic acid construct containing a gene of a DNA binding protein of Dof family having the above-described properties to express the gene of the DNA binding protein of Dof family in the transformed plant. In a particularly preferred embodiment, maize Dof1 protein and the gene thereof are used. As described above, the maize Dof1 factor was found as a DNA binding protein being able to bind to the promoter region of the gene of maize C4 phosphoenolpyruvate carboxylase which was originally found as the first protein of Dof family. It was further elucidated that the Dof1 factor has a property of enhancing the transcription of C4 and C3 phosphoenolpyruvate carboxylase (PEPC) gene and also the property of the transcription of cytoplasmic pyruvate ortho-phosphate dikinase (PPDK) gene. This fact indicates that Dof1 does not control the expression of a single gene but it simultaneously controls the expression of two or more genes to play the physiological roles thereof. On the other hand, phosphoenolpyruvate carboxylase and cytoplasmic pyruvate o-phosphate dikinase together function on the basis of the above-described enzymatic activity to supply the carbon backbones to the TCA cycle. As a result, the generation of 2-oxoglutaric acid which accepts nitrogen (ammonia) is accelerated. Namely, it is considered that the protein/gene which supply the abundant carbon backbones into TCA cycle, particularly the protein/gene which supply the abundant carbon backbones to 2-oxoglutaric acid, functions as a master control protein/gene in the carbon providing pathway and that the carbon supply into the nitrogen (ammonia) assimilation system is positively controlled by the protein/gene. By such a positive control of the carbon supply by the function of such protein/gene, an increase of free amino acid content in plants may be expected. Further, as a result of the metabolic modification, an increase of nitrogen content of the plant is also expected. Further, the tolerance to nitrogen deficiency is expected.

The term "master control protein in carbon providing pathway" herein indicates a group of proteins which regulate the metabolic pathway leading to 2-oxoglutaric acid, in particular, a group of proteins which control the metabolic pathway leading from triose to 2-oxoglutaric acid in the glycolysis and subsequent TCA cycle.

Thus, the DNA binding protein belonging to Dof family used in the present invention is not limited to Dof1 derived from maize. It may be any Dof family DNA binding proteins derived from another kind of plants so far as they function as the master control proteins in the carbon providing pathway. Further, a Dof family DNA binding protein where one or more amino acids are deleted, replaced or added can also be used in the present invention so far as it has the above-described function. In view of the role as a master control gene/protein and also in view of the fact that the present investigation revealed that maize Dof1 actually functions in Arabidopsis thaliana, it is considered that DNA binding proteins of Dof family and genes thereof exhibit the equivalent function in an intended plant even when the proteins and genes are derived from other species of plants. The expression "having a function equivalent to that of maize Dof1" herein indicates that it has a function of accelerating the transcription of phosphoenol pyruvate carboxylase gene and/or cytoplasmic pyruvate ortho-phosphate dikinase gene.

The genes of the Dof family or cDNA thereof can be relatively easily prepared according to the published sequence information thereof For example, the nucleotide sequence of cDNA of maize Dof1 gene is published, as Genbank accession No. X66076. Dof1 cDNA can be relatively easily obtained by synthesizing PCR primers base on this sequence so that DNA fragment containing the region encoding the protein and carrying out RT-PCR by using RNA extracted from maize leaves as a template. As for the Dof family genes of *Arabidopsis thaliana*, DNA binding protein belonging to Dof family was already annotated on the basis of the data of the complete genome sequence of *Arabidopsis thaliana* [published by, for example, Kazusa DNA Research Institute KAOS and National Center for Biotechnology Information, USA]. The cDNA fragment can be obtained by the similar method based on such information. For soybeans, potatoes, tomatoes and pumpkins, EST having Dof motif is disclosed in database [see, for example, National Center for Biotechnology Information, USA]. It is easy to obtain the full-length cDNA on the basis of such sequence information by experimental procedures well known in the art. It is also possible to obtain Dof family DNA binding protein genes from relative plant species (Gramineae, Cruciferae, Leguminosae, Solanaceae and Cucurbitaceae) starting from the cDNA using cross hybridization technique. Whether the Dof family genes thus obtained is practically usable for the purpose of the present invention or not can be relatively easily examined by introducing the gene into a plant and examining the change in the mRNA level of phosphoenolpyruvate carboxylase gene andlor cytoplasmic pyruvate ortho-phosphate dikinase gene andlor the change in the amount of the expression at the protein level, and the change in the size of the plant, which are used as the indicators.

The nucleic acid constructs used in the present invention can be generated by the methods well known in the art. As for the molecular biological techniques for isolating the nucleic acid construct and determining the sequence thereof, literatures such as Sambrook, et al., "Molecular cloning-Laboratory manual", $2^{nd}$ edition (Cold Spring Harbor Laboratory Press) can be referred to. For the gene amplification by PCR method or the like which may be required in some cases for the production of the nucleic acid constructs usable in the present invention, "Current Protocols in Molecular Biology" edited by F. M. Ausubel, et al. (eds.) and published by John Wiley & Sons, Inc. (1994) can be referred to.

The nucleic acid constructs usable in the present invention may generally contain a suitable promoter, which functions in plant cells, such as nopaline synthase gene, 35S promoter of cauliflower mosaic virus (CaMV35S), a suitable terminator such as the terminator of nopaline synthase gene, other sequences necessary or advantageous for the expression, and a marker gene for selecting the transformant such as a drug resistant gene, e.g. kanamycin resistant gene, G418 or hygromycin.

The promoter usable for the constructs may be either a constitutive promoter or an organ-specific or growing stage-specific promoter. Such promoters can be selected depending on the host to be used, the required expression level, the organ in which the expression is particularly intended or the growing stage. In a preferred embodiment of the present invention, a strong promoter such as CaMV35S promoter, which expresses non-specifically to the organ or growing stage is used. The promoters specific to organs include phaseolin gene promoter, patatin gene promoter, etc. In the most preferred embodiment of the present invention, a construct is used wherein the PEPC gene is driven by a powerful constitutive promoter such as CaMV35S promoter.

The method for introducing the genes is not particularly limited in the present invention. Any method for introducing genes into plant cells or into the plant body, known by those skilled in the art, can be selected depending on the host. For example, in one embodiment of the present invention, the gene introduction by *Agrobacterium* method can be employed. In such a transforming system, a binary vector is preferably used. When *Agrobacterium* is used, the nucleic acid construct used for the transformation further contains T-DNA flanking the DNA sequence to be introduced into plant cells. In a preferred embodiment, the introduced sequence is inserted between the left and right T-DNA border sequences. The suitable design and construction of such transforming vectors based on T-DNA are well known in the art. Further, the conditions necessitated for the infection of a plant with *Agrobacterium* having such a nucleic acid construct are also well known in the art. As for such techniques and conditions, "Model Shokubutsu no Jikken Protocol; Ine, Shiroinunazuna (Experiment Protocol for Model Plants; Rice Plants and *Arabidopsis thaliana*) (1996) can be referred to.

In the present invention, other gene transfer methods can also be used. Examples of the gene transfer methods which can be employed herein include a method for introducing DNA into a protoplast with polyethylene glycol and calcium, a method for transformation of a protoplast by electroporation, a particle gun method, etc.

Although the species of plants to be subjected to such genetic manipulation are not particularly limited as described above, the plants which are easily transformed, and the regeneration systems of which have been established are preferred when the plant bodies per se are used for the transformation. In addition to the plants having the above-described characteristic properties, species of plants for which a large scale cultivation technique has been established are preferred in the present invention from the view point of the efficient use of the produced amino acids. Plants suitable for the method of the present invention include, for example, all the plants of Cruciferae as well as tomato, potato, maize, wheat, rice plant, sugarcane, soybean and sorghum. The organs and cells that are subjected to the above-described genetic manipulation are not particularly limited, and they can be selected depending on the host, gene introducing method, etc. Examples of them include, but are not limited to, organ explants, pollens, cultured cells, embryos and plant bodies.

Then the transformants may be selected from the plant cells and the like manipulated as described above. The selection can be based on the expression of the marker gene present on the nucleic acid construct used for the transformation. For example, when the marker gene is drug resistant gene, the selection can be conducted by culturing or growing manipulated plant cells et al. on a culture medium containing a suitable concentration of the antibiotic or herbicide. When the marker gene is β-glucuronidase gene, luciferase gene or the like, the transformants can be selected by screening for their activity. It is also possible to select the transformants on the basis of the increase in the transcription level of the phosphoenol pyruvate carboxylase gene and/or the cytoplasmic pyruvate o-phosphate dikinase gene, or on the basis of the increase in the amount of protein in the phosphoenol pyruvate carboxylase and/or the cytoplasmic pyruvate ortho-phosphate dikinase as an indicator. In particular, the increase in the transcription level/protein level in the phosphoenol pyruvate carboxylase gene and cytoplasmic pyruvate ortho-phosphate dikinase gene can be employed as an indicator for confirming that the introduced Dof family gene or its modified version can be used for the purpose of the present invention or not.

When thus identified transformants are not plant bodies, in other words, when they are protoplasts, calli or explants and the like, the regeneration thereof into plant bodies may be carried out. For the regeneration, the methods known by those skilled in the art for each host plant may be employed.

The plants thus obtained can be cultured by an ordinary method or, in other words, under the same conditions as those for the untransformed plants. For the identification of the transformed plants containing the nucleic acid constructs of the present invention, various molecular biological methods can be employed in addition to the above-described selection based on the marker gene. For example, Southern hybridization or PCR may be employed for detecting the inserted recombinant DNA fragments and also the structure thereof. Northern hybridization or RT-PCR can be employed for detecting and determining RNA transcripts from the introduced nucleic acid construct.

On the other hand, the seedlings of transformed plants containing Dof1 tend to have darker green leaves than those of untransformed plants and the size of the former plants is inclined to be smaller than that of the latter plants. A positive correlation is recognized between the degree of the smallness in size and the expression level of introduced Dof1. Accordingly, it is possible to select the transformed plants in which the Dof family gene has been introduced and the introduced Dof family gene is expressed, at the initial stage of the growth by using such phenotypes as the indicators in combination with the above-described analysis for drug-resistance and enzymatic activity. It is also possible to confirm that the introduced gene meets the purpose of the present invention by employing such a phenotype as the indicator.

The expression of the Dof family DNA binding protein gene in the obtained transformant may be then evaluated on the basis of the amount of this protein, the amount of mRNA or the expression level of the target gene (phosphoenol pyruvate carboxylase gene or cytoplasmic pyruvate ortho-phosphate dikinase gene) for the introduced gene. For example, the amount of the Dof family DNA binding protein may be determined by Western blotting method or the like, and the amount of mRNA may be determined by Northern blotting method or quantitative RT-PCR method. The transcriptional control activity of the Dof family DNA binding protein can be evaluated by determining the amount of mRNA of the target gene (phosphoenol pyruvate carboxylase gene or cytoplasmic pyruvate ortho-phosphate dikinase gene) in the similar manner as that described above. These methods are well known in the art, and kits for easily performing them are also commercially available. The transformed plant in which the expression of Dof family DNA binding protein gene was confirmed is then examined to determine whether it is the plant having either the properties of "enhanced amino acid content", "enhanced nitrogen content" or tolerance to nitrogen deficiency".

The "enhanced amino acid content" may be determined by the contents of free amino acids in the plant body. The free amino acid content can be examined by, for example, crushing the whole or a part of the transformed plant, obtaining an extract therefrom and examining the extract with an amino acid analyzer. A transformed plant is the "plant having an enhanced amino acid content" of the present invention when the transformed plant has a higher free amino acid content than that of the wild strain.

The "enhanced nitrogen content" is determined on the basis of the total nitrogen content of the plant body. The total nitrogen content may be determined by, taking the whole or a part of the transformed plant body and determining the nitrogen content with an NC analyzer. A transformed plant is the "plant having an enhanced plant nitrogen content" of the present invention when the transformed plant has a higher total nitrogen content than that of the wild strain.

The "tolerance to nitrogen deficiency" is examined by growing a plant on a medium having a reduced nitrogen content and observing the growth thereof. To know whether the plant is tolerant to nitrogen deficiency or not, the plant is grown on a medium having a standard nitrogen content or on a medium having a nitrogen content containing as low as $1/25$ of the standard nitrogen content or the plant is grown on an ordinary soil or another soil having a nitrogen content as low as $1/25$ of that of the ordinary soil, and then the fresh weight or dry weight of the plant body is determined. When the degree of the reduction in fresh weight or dry weight of the plant obtained by growing on the medium having the reduced nitrogen content or on the soil having the reduced nitrogen content is lower than the degree of weight reduction in the wile type plant, it is considered that the plant is tolerant to nitrogen deficiency. The transformed plant that grows better than the wild type plant under limited nitrogen is the "plant tolerant to nitrogen deficiency" of the present invention.

Once the transformed plant having an enhanced free amino acid content and/or the transformed plant having enhanced nitrogen content and/or the transformed plant tolerant to nitrogen deficiency is thus identified, the plant may be then examined whether its properties can be genetically stably maintained. For the examination, the plant may be grown or cultivated under ordinary conditions, the seeds are taken from them and the properties and the segregation in the descendants thereof is analyzed. The presence or absence of the induced nucleic acid constructs, the location thereof and the expression thereof in the progenies can be analyzed in the similar manner as that for the primary (T1 generation) transformants.

The transformed plants having an enhanced free amino acid content and/or the transformed plant having an enhanced nitrogen content and/or the transformed plant tolerant to nitrogen deficiency may be either hemizygous or homozygous for the sequence derived from the nucleic acid constructs integrated into the genome. If necessary, both of the hemizygotes and homozygotes can be obtained by mating the progenies. The sequences derived from the nucleic acid constructs integrated into the genomes may segregate according to Mendelism in the progenies. Therefore, for obtaining the descendant plants and seeds thereof, it is preferred to use homozygous plants from the viewpoint of the stability of the properties.

The foreign gene may be inserted into a single locus in the transformant in many cases, although it is not rare that the transformant is a multi-copy transformant in which the foreign gene is inserted into plural loci. A single copy transformant is preferred in the present invention because of the stability of the introduced gene. For example, a transformant having a gene introduced into a single locus, i.e. a single copy transformant, can be selected by examining the segregation ratio of kanamycin resistance in T2 (the second generation). When T1 is hemizygous and the gene has been introduced into a single locus, the kanamycin resistant and the kanamycin segregate at the ratio of 3:1 in T2 generation, according to Mendel's law. When the introduced gene exists as multi-copy, the frequency of the resistant transformant will be increased. Accordingly, the single copy transformant can be obtained by seeding the obtained T2 seeds on kanamycin-containing medium, and selecting the line which segregate at the ratio of 3:1 to select the transformant, which indicate that the gene is considered to be inserted in a single locus.

The transformed plants thus obtained may be grown under the same cultivation conditions as those of the natural plants of the same species to provide the crops having an enhanced amino acid content. Further, by using even a smaller amount of nitrogen fertilizer, crops may be obtained in an amount equal to that obtained by using an ordinary amount of nitrogen fertilizer. The seeds may be also obtained from the transformed plants thus obtained. The seeds may be easily obtained by the same method as that for the same, non-transformed plants. If necessary, the obtained seeds may be stored, sterilized or treated with pesticides by a well-known, ordinary method.

EXAMPLES

Example 1

Introduction of Maize Dof1 Gene into Plant Transforming Vector

The introduction of Dof1 gene from 35SC4PPDK-Dof1-HA plasmid (The Plant Cell 1998, 10 (Jan.), 75-89) into the plant transforming vector pBI121 (Clontech Co.) was carried out as follows:

35SC4PPDK-Dof1-HA plasmid has the DNA segment in which the domain ranging from TATA box to the translation initiation site of maize C4 pyruvate ortho-phosphate dikinase gene and Dof1cDNA are connected downstream of Cauliflower Mosaic Virus 35S enhancer and further, two molecules of phytohemagglutinin cDNA are connected in tandem as the epitope tag at the downstream thereof and the termination site of nopaline synthase is connected at the end. The DNA segment may be isolated by double digestion with restriction enzymes XhoI and EcoRI. Then, the XhoI-EcoRI fragment was inserted into T-DNA domain of pBI121. At first, pBI121 was cleaved by HindIII, and the end was blunted using Cloned Pfu DNA polymerase (Stratagene Co.). Then, after connecting phosphorylated XhoI linker (Takara Shuzo Co., Ltd.) using T4 DNA ligase (Takara Shuzo Co., Ltd.) followed by digestion with XhoI, the linker fragments were removed by gel filtration with MicroSpin Column S-300 (Amersham-Pharmacia Co.). The obtained product was self-cyclized using T4 DNA ligase to obtain the plasmid having XhoI site in place of HindIII site. Thus, the obtained plasmid had XhoI and EcoRI as the unique sites. The plasmid thus obtained was cleaved by XhoI and EcoRI and the XhoI-EcoRI fragment of 35SC4PPDK-Dof1-HA which had been separately prepared was introduced therein to obtain pBI121 Dof1 (FIG. 1A).

Example 2

Introduction of Maize Dof1 Gene into *Arabidopsis thaliana*

Plasmid pBI121Dof1 was introduced into *Agrobacterium* C58C1Rif by triparental mating using *E. coli* containing pBI121Dof1 and helper *E. coli* HB101/pRK203. The obtained *Agrobacterium* C58C1Rif harboring pBI121Dof1 was used to infect *Arabidopsis thaliana* Columbia by vacuum infiltration method. The vacuum infiltration was conducted by the method described in "*Model Shokubutsu no Jikken Protocol: Ine, Shiroinunazuna Hen* (Experiment Protocol for Model Plants: Edition of Rice Plants and *Arabidopsis thaliana*)" (1996) in the special number of "*Saibo Kogaku* (Cell Technology)" (published by Shujunsha). The seeds (T1) obtained from the infected plants were planted on GM agar medium [1×MS, 1×B5 vitamin, 10 g/l sucrose, 0.5 g/l MES-KOH (pH 7.5) and 0.8% agar] containing 100 mg/ml of kanamycin after the sterilization with sodium hypochlorite solution having an effective chlorine concentration of 1%, and the transformants were screened.

The T2 seeds were obtained from the resultant transformant (T1 generation) and again planted on the kanamycin-containing medium, and the lines having the segregation ratio of 3:1 were selected, and the transformants in which the gene is considered to be located in a single locus were selected. As a result, three kanamycin-resistant lines were obtained from 121Dof1.

Example 3

Analysis of the Genomic DNA of *Arabidopsis thaliana* Having Maize Dof1 Gene Introduced Thereinto Genomic DNAs of the three kanamycin-resistant lines were analyzed to confirm the presence of Dof1 gene. As for the transformant, the seeds of T2 or T3 generation were planted on Murashige and Skoog medium containing 100 mg/l of kanamycin and the seedlings were grown to prepare the materials for preparing the genome DNAs. The genome DNAs were isolated from *Arabidopsis thaliana* using DNeasy Plant Kit (QIAGEN Co.). PCR was carried out by using the obtained DNA as a substrate with the primer annealing to the 5'-upstream of 35S promoter:

35S-5Pro5' (5'-TTCCATTGCCCAGCTATCTGTCACTT-3') (SEQ ID NO: 1) and the primer annealing to the 3'-downstream of nopaline synthase terminator:

NOS-Ter3' (5'-TCATCGCMGACCGGCMCAGGATTC-3') (SEQ ID NO: 2).

Figure 1B:
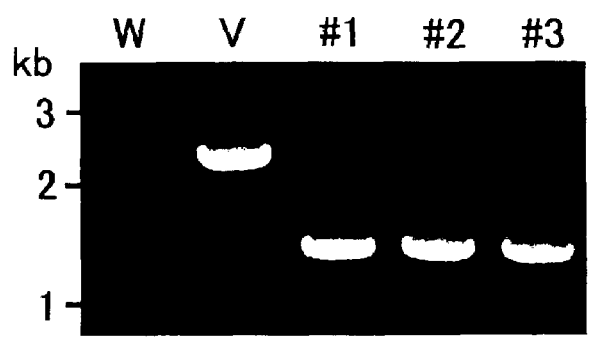
FIG. 1B shows the results of the genome DNA analysis of Arabidopsis thaliana containing Dof1 gene, wherein W represents wild type, V represents the control plant transformed with only vector, and #1 to #3 represent a transformed plant having 121 Dof1 introduced therein, respectively.

The results are shown in FIG. 1B. In FIG. 1B, W represents the wild type plant (Columbia), V represents the control plant transformed only with the vector (pBI121) and #1 through #3 represent three transformed plant lines obtained by the introduction of 121Dof1.

In V, about 2.2 kb of amplified fragment containing β-glucuronidase gene should be obtained. Because Dof1 gene is about 750 bp, the amplified fragment was supposed to be about 1.3 kb for Dof1 transformants. In fact, the fragment having an estimated size was obtained, and it was confirmed that Dof1 gene had been introduced into the transformants.

Example 4

Analysis of RNA of Dof1 Transformants

RNA analysis of the obtained transformants was further conducted so as to confirm the expression of Dof1 gene. Total RNA was isolated from the seedlings of *Arabidopsis thaliana*, prepared as described above, using Trizol reagent (Gibco BRL Co.). Dof1 mRNA was detected by RT-PCR carried out with superscript II (Gibco BRL Co.) and TaKaRa Ex taq (Takara Shuzo Co., Ltd.) using the obtained RNA as a template. The primers used for Dof1 were:

ZMDof1-A (5'-CCCAGCGCCGTCGCGCATGCAGG-3') (SEQ ID NO: 3) and NOS-Ter-3' (sequence No. 2) which was homologous to the sequence of NOS terminator located just downstream of the translation region of Dof1. As a positive control for RT-PCR, β-tubulin mRNA was also amplified. The primers were as follows:

b-At-tubulin-5' (5'-CTCGTGGATCACAGCAATACA-GAGCC-3') (SEQ ID NO: 5) and b-At-tubulin-3' (5'-TCCTCCTGCACTTCCACT-TCGTCTTC-3') (SEQ ID NO: 6).

Figure 1C:
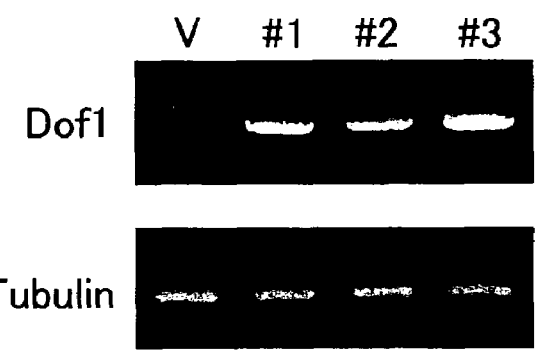
FIG. 1C shows the results of RNA analysis of a transformed plant having Dof1 introduced thereinto, wherein V and #1 to #3 are as defined in FIG. 1(B).

The results of the analysis are shown in FIG. 1C.

As shown in FIG. 1C, the amplification of RT-PCR product was observed only in the transformants when Dof1 primers were used. From these results, it was confirmed that the expression of Dof1 gene is peculiar to the transformants.

Example 5

Analysis of the Expression of Phosphoenol Pyruvate Carboxylase Gene and Cytoplasmic Pyruvate Ortho-phosphate Dikinase Gene in Dof1 Transformants of *Arabidopsis thaliana*

To confirm whether the expressed Dof1 functions or not, the expression of endogenous phosphoenol pyruvate carboxylase gene and cytoplasmic pyruvate ortho-phosphate dikinase gene in *Arabidopsis thaliana* was analyzed. RT-PCR was carried out by using the above-described total RNA as the substrate and the groups of the following primers corresponding to two kinds of PEPC genes among the plural phosphoenol pyruvate carboxylase (PEPC) genes locating on the genome:

AtPEPC1-5' (5'-GGTTTCGGAGCAGCATTTAGGTATGC-3') (SEQ ID NO: 7) and
AtPEPC1-3' (5'-TTMCCGGTGTTTTGCMTCCTGCAG-3') (SEQ ID NO: 8), or
AtPEPC2-5' (5'-MCCMTGGCCATTCMCCGTGTCAC-3') (SEQ ID NO: 9) and
AtPEPC2-3' (5'-TTAACCGGTGTTTTGCATACCAGCAG-3') (SEQ ID NO: 10), or the primers corresponding to cytoplasmic pyruvate ortho-phosphate dikinase (cyPPDK) gene:
At-cyPPDK-5' (5'-ATGATGCAGCGAGTATTCAC-CTTTGG-3') (SEQ ID NO: 11) and
At-cyPPDK-3' (5'-AGCGAGGGMGCTCCAATGT-CACGTT-3') (SEQ ID NO: 12), or the primers corresponding to ferredoxin type glutamate synthetic enzyme gene (GLU1):
AtGLU1-5' (5'-ATGACTGGTGGCTGTGTAGTCGTGCT-3') (SEQ ID NO: 13) and
AtGLU1-3' (5'-CMCTGCCACAACCTGCTCTTGAATG-3') (SEQ ID NO: 14), or the primers corresponding to chloroplast-localized glutamate synthetic enzyme gene (CS2):
AtGS2-5' (5'-ATGGCTCAGATCTTAGCAGCTTCTCC-3') (SEQ ID NO: 15) and
ATGS2-3' (5'-ATCACTTCACTATCTTCACCAGGTGC-3') (SEQ ID NO: 16). Then, the expression of each gene was evaluated.

Figure 2:
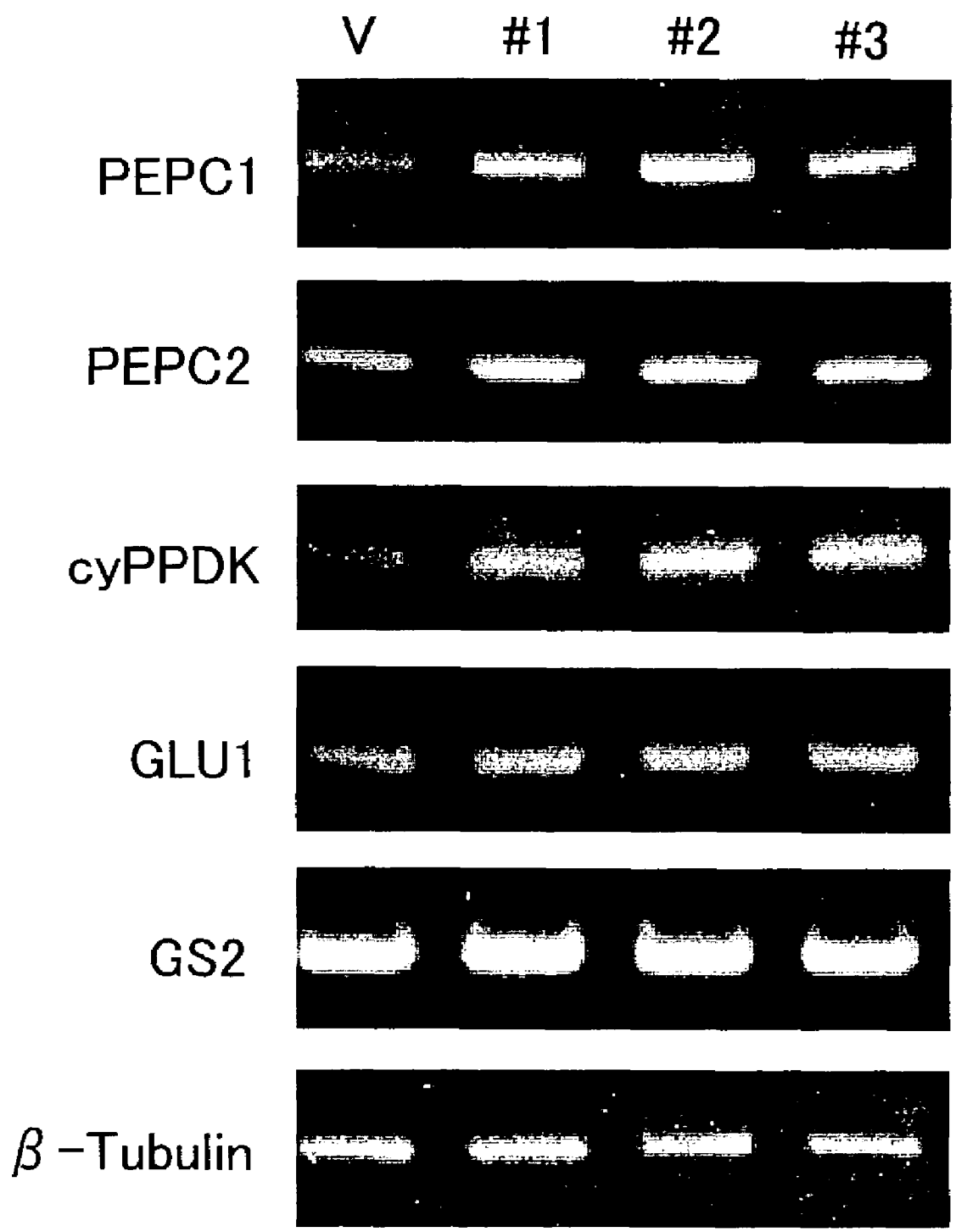
FIG. 2 shows the results of the analysis of the expression of PEPC and cyPPDK genes in a transformed plant having Dof1 introduced thereinto, wherein V and #1 to #3 are as defined in FIGS. 1(A) and 1(B).

As a result, an increase in the expression was observed for PEPC and cyPPDK, and no influence was observed on the expression of GLU1 and GS2 (FIG. 2). These results show that the introduced Dof1 gene is expressed in the cells of *Arabidopsis thaliana* and that the product thereof functions in the same manner as in maize cells.

Example 6

Amino Acid Analysis of *Arabidopsis thaliana* Having Maize Dof1 Gene Introduced Thereinto The amino acid analysis of thus transformed *Arabidopsis thaliana* was carried out.

Seeds of *Arabidopsis thaliana* were planted on PNS medium containing 5 mM $KNO_3$, 2.5 mM $KH_2PO_4$, 2.0 mM $MgSO_4$, 2.0 mM $Ca(NO_3)_2$, 0.05 mM Fe-EDTA, 0.07 mM $H_3BO_3$, 0.014 mM $MnCl_2$, 0.0005 mM $CuSO_4$, 0.001 mM $ZnSO_4$, 0.0002 mM $Na_2MOO_4$, 0.01 mM NaCl, 0.00001 mM $CoCl_2$ (pH: adjusted to 5.5 with KOH) and 0.8% agar, or on a medium comprising ½ MS medium which contains the salts in an amount of ½ of those in Murashige and Skoog (MS) medium described in "*Model Shokubutsu no Jikken Protocol; Ine, Shiroinunazuna Hen* (Experiment Protocol for Model Plants; Edition of Rice Plants and *Arabidopsis thaliana*)" (1996) in a special number of "*Saibo Kogaku* (Cell Technology)" (published by Shujunsha) supplemented with or without 10 g/l sucrose. The seeds were cultivated under long-day conditions comprising 16 hours of light period and 8 hours of dark period at 22° C. for about 2 weeks to obtain the seedlings having about 5 or 6 true leaves. When the transformants were to be grown, 100 mg/l of kanamycin was added to the medium.

The obtained seedlings were crushed in liquid nitrogen by using a mortar and pestle and were extracted with 80% ethanol at 70° C. Oil-soluble components were removed by the extraction with 80% ethyl ether. The aqueous layer was freeze-dried and then dissolved in 10 mM HC to obtain the samples for amino acid analysis. The content of each free amino acid in the sample was determined by using amino acid analyzer LC 8800 (Hitachi, Ltd.).

Figure 3A:
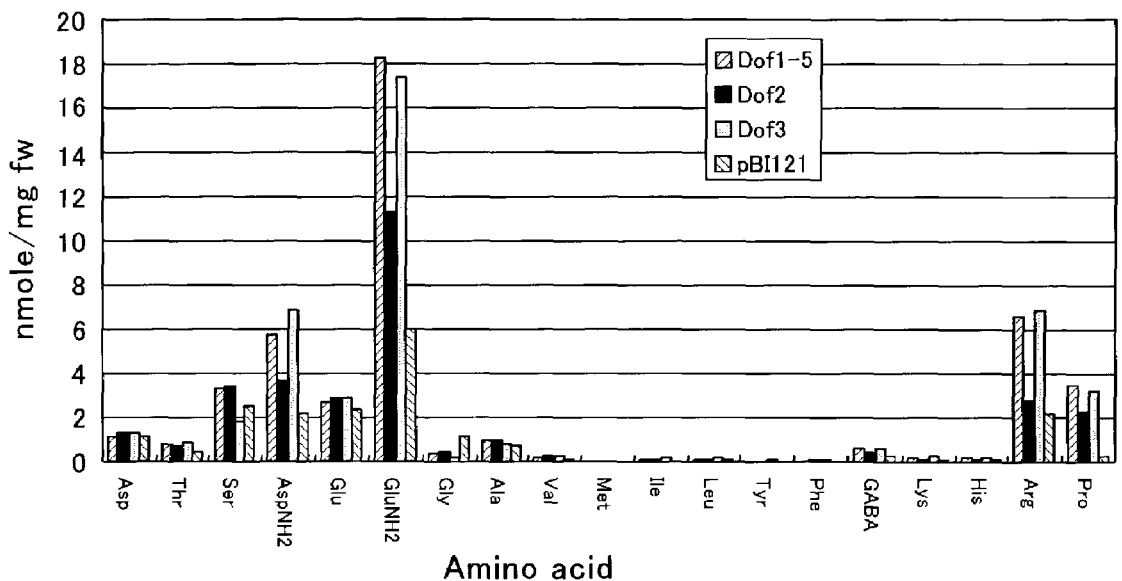
FIG. 3A shows the results of the amino acid analysis of Dof1-introduced transformed plants: The amino acid contents of transformed plants having Dof1 introduced thereinto, which were grown in ½ MS medium.
Figure 3B:
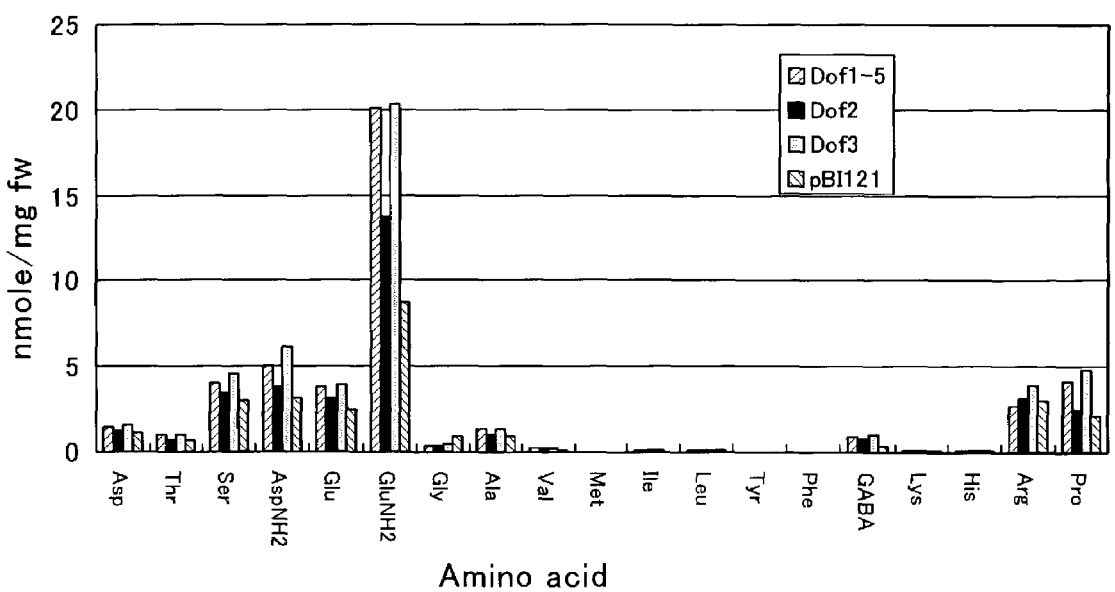
FIG. 3B shows the results of the amino acid analysis of Dof1-introduced transformed plants: The amino acid contents of transformed plants having Dof1 introduced thereinto, which were grown in ½ MS medium containing 10 g/l of sucrose.
Figure 4A:
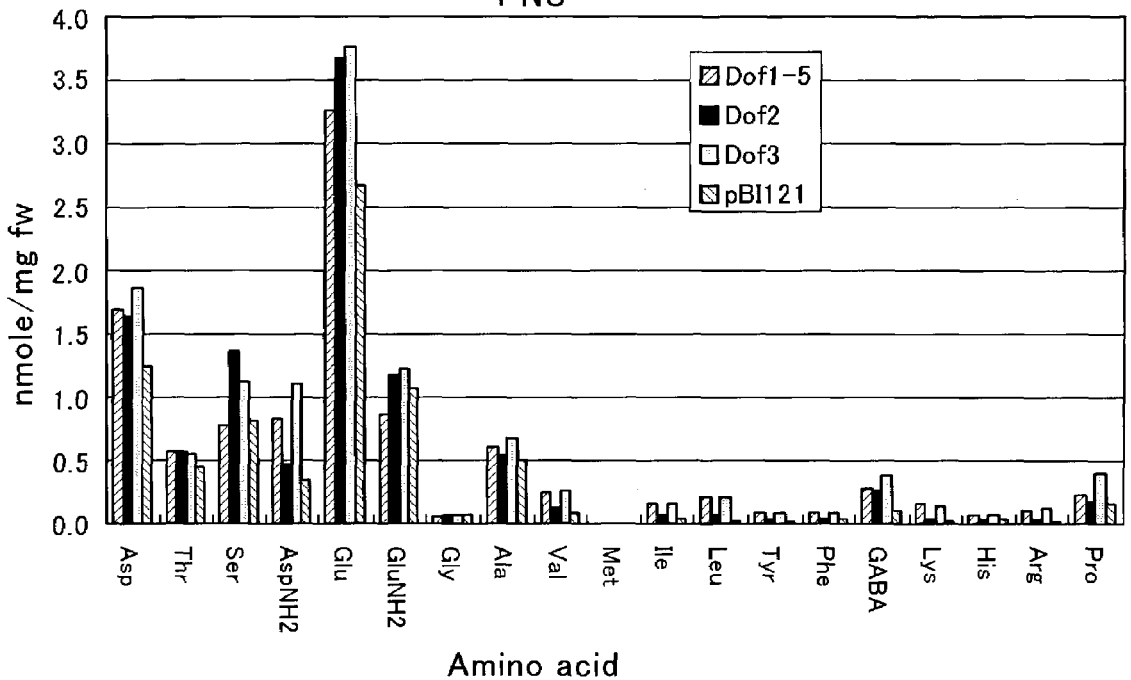
FIG. 4A shows the amino acid contents of transformed plants having Dof1 introduced thereinto, which were grown in PNS medium.
Figure 4B:
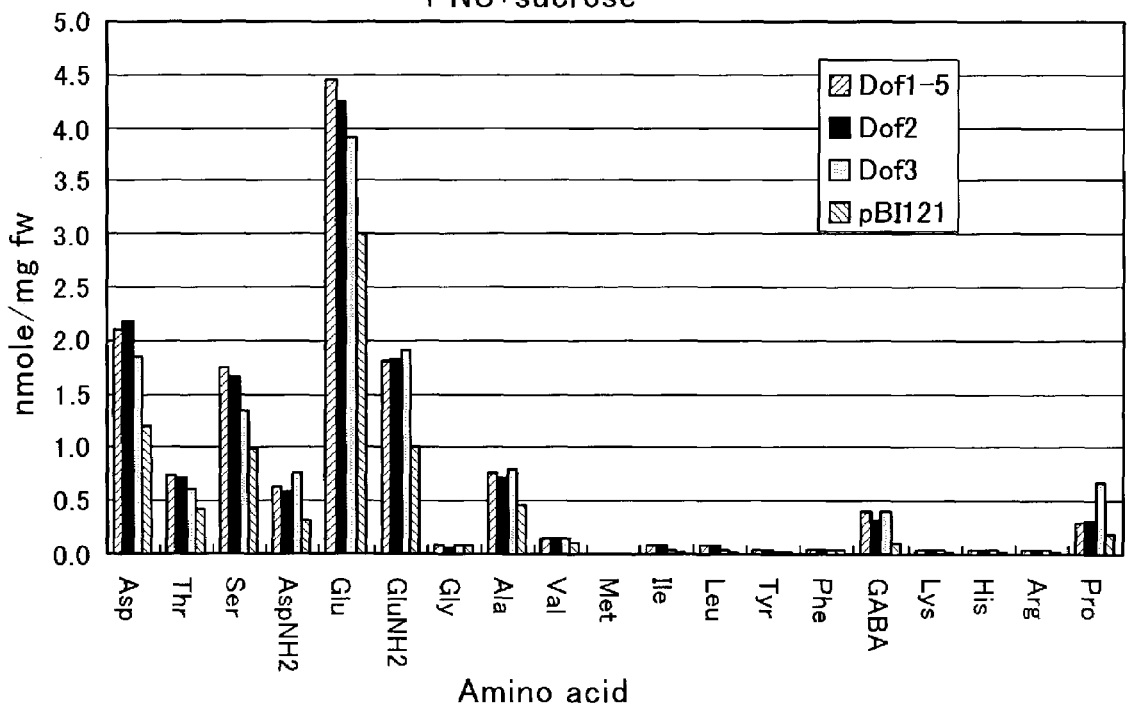
FIG. 4B shows the amino acid contents of transformed plants having Dof1 introduced thereinto, which were grown in PNS medium containing 10 g/l of sucrose.

The typical results thus obtained are shown in Tables 1 to 4 and FIGS. 3 and 4.

TABLE 1

Amino acid contents of transfermed plant grown in 1/2 MS medium (nmole/gFW)

|  | V | #1 | #2 | #3 |
|---|---|---|---|---|
| Asp | 1.0992 | 1.0874 | 1.3122 | 1.2650 |
| Thr | 0.4600 | 0.7957 | 0.6578 | 0.8906 |
| Ser | 2.5074 | 3.2793 | 3.3666 | 1.8181 |
| $AspNH_2$ | 2.2042 | 5.7036 | 3.6604 | 6.8509 |
| Glu | 2.3505 | 2.7318 | 2.9078 | 2.8923 |
| $GluNH_2$ | 6.0014 | 18.2261 | 11.3421 | 17.4071 |
| Gly | 1.1302 | 0.3157 | 0.4539 | 0.1498 |
| Ala | 0.6598 | 0.9273 | 0.9786 | 0.8006 |
| Val | 0.1269 | 0.2168 | 0.2194 | 0.3013 |
| Met | 0.0073 | 0.0112 | 0.0093 | 0.0092 |
| Ile | 0.0357 | 0.0653 | 0.0737 | 0.1539 |
| Leu | 0.0461 | 0.0792 | 0.0885 | 0.1876 |
| Tyr | 0.0180 | 0.0295 | 0.0357 | 0.0716 |
| Phe | 0.0392 | 0.0425 | 0.0598 | 0.0897 |
| GABA | 0.2570 | 0.6150 | 0.4583 | 0.06342 |
| Lys | 0.0584 | 0.1514 | 0.1168 | 0.2515 |
| His | 0.0768 | 0.1759 | 0.1303 | 0.1966 |
| Arg | 2.1794 | 6.6168 | 2.7871 | 6.8635 |
| Pro | 0.3017 | 3.4517 | 2.2233 | 3.2131 |
| total | 19.5593 | 44.5222 | 30.8817 | 44.0466 |

TABLE 2

Amino acid contents of transformed plant growth in 1/2 MS medium containing 10 g/l of sucrose (nmole/gFW)

|  | V | #1 | #2 | #3 |
|---|---|---|---|---|
| Asp | 1.0936 | 1.4753 | 1.1762 | 1.5386 |
| Thr | 0.6733 | 0.9895 | 0.6932 | 0.9731 |
| Ser | 3.0501 | 4.0631 | 3.4961 | 4.6288 |
| $AspNH_2$ | 3.1797 | 5.0051 | 3.7775 | 6.1035 |
| Glu | 2.4713 | 3.8162 | 3.1327 | 3.8936 |
| $GluNH_2$ | 8.7008 | 20.1444 | 13.7146 | 20.3577 |

TABLE 2-continued

Amino acid contents of transformed plant growth in 1/2 MS medium containing 10 g/l of sucrose (nmole/gFW)

|  | V | #1 | #2 | #3 |
|---|---|---|---|---|
| Gly | 0.8886 | 0.3394 | 0.2863 | 0.4535 |
| Ala | 0.8556 | 1.3261 | 0.9843 | 1.3008 |
| Val | 0.1591 | 0.2258 | 0.1906 | 0.2195 |
| Met | 0.0048 | 0.0163 | 0.0075 | 0.0138 |
| Ile | 0.0472 | 0.0620 | 0.0607 | 0.0566 |
| Leu | 0.0655 | 0.0734 | 0.0749 | 0.0706 |
| Tyr | 0.0226 | 0.0363 | 0.0341 | 0.0356 |
| Phe | 0.0501 | 0.0410 | 0.0423 | 0.0428 |
| GABA | 0.3263 | 0.9097 | 0.7846 | 0.9582 |
| Lys | 0.0931 | 0.1013 | 0.1101 | 0.1145 |
| His | 0.1103 | 0.1451 | 0.1381 | 0.1507 |
| Arg | 2.9603 | 2.6554 | 3.0932 | 3.8730 |
| Pro | 2.1760 | 4.1317 | 2.5110 | 4.7840 |
| total | 26.9282 | 45.5672 | 34.3080 | 49.5690 |

TABLE 3

Amino acid contents of transformed plant grown in PNS medium (nmole/gFW)

|  | V | #1 | #2 | #3 |
|---|---|---|---|---|
| Asp | 1.2453 | 1.6919 | 1.6326 | 1.8683 |
| Thr | 0.4447 | 0.5701 | 0.5679 | 0.5553 |
| Ser | 0.8143 | 0.7806 | 1.3598 | 1.1219 |
| AspNH$_2$ | 0.3430 | 0.8309 | 0.4614 | 1.0996 |
| Glu | 2.6759 | 3.2601 | 3.6798 | 3.7597 |
| GluNH$_2$ | 1.0750 | 0.8552 | 1.1715 | 1.2209 |
| Gly | 0.0733 | 0.0521 | 0.0621 | 0.0683 |
| Ala | 0.4919 | 0.6035 | 0.5332 | 0.6760 |
| Val | 0.0885 | 0.2463 | 0.1189 | 0.2629 |
| Met | 0.0042 | 0.0038 | 0.0042 | 0.0050 |
| Ile | 0.0266 | 0.1593 | 0.0685 | 0.1637 |
| Leu | 0.0251 | 0.2063 | 0.0692 | 0.2071 |
| Tyr | 0.0130 | 0.0823 | 0.0395 | 0.0819 |
| Phe | 0.0385 | 0.0858 | 0.0382 | 0.0836 |
| GABA | 0.1073 | 0.2753 | 0.2670 | 0.3722 |
| Lys | 0.0189 | 0.1466 | 0.0332 | 0.1387 |
| His | 0.0288 | 0.0730 | 0.0420 | 0.0756 |
| Arg | 0.0197 | 0.1011 | 0.0308 | 0.1140 |
| Pro | 0.1472 | 0.2201 | 0.1792 | 0.3979 |
| total | 7.6812 | 10.2442 | 10.3591 | 12.2727 |

TABLE 4

Amino acid contents of transformed plant grown in PNS medium containing 10 g/l of sucrose (nmole/gFW)

|  | V | #1 | #2 | #3 |
|---|---|---|---|---|
| Asp | 1.2074 | 2.1052 | 2.1766 | 1.8427 |
| Thr | 0.4291 | 0.7338 | 0.7065 | 0.5996 |

TABLE 4-continued

Amino acid contents of transformed plant grown in PNS medium containing 10 g/l of sucrose (nmole/gFW)

|  | V | #1 | #2 | #3 |
|---|---|---|---|---|
| Ser | 0.9887 | 1.7463 | 1.6701 | 1.3512 |
| AspNH$_2$ | 0.3197 | 0.6216 | 0.5816 | 0.7635 |
| Glu | 2.9957 | 4.4517 | 4.2362 | 3.9115 |
| GluNH$_2$ | 0.9979 | 1.8168 | 1.8343 | 1.9038 |
| Gly | 0.0756 | 0.0752 | 0.0692 | 0.0795 |
| Ala | 0.4561 | 0.7649 | 0.7121 | 0.8029 |
| Val | 0.0978 | 0.1567 | 0.1510 | 0.1460 |
| Met | 0.0020 | 0.0051 | 0.0029 | 0.0048 |
| Ile | 0.0297 | 0.0812 | 0.0835 | 0.0438 |
| Leu | 0.0300 | 0.0903 | 0.0910 | 0.0484 |
| Tyr | 0.0151 | 0.0477 | 0.0437 | 0.0261 |
| Phe | 0.0395 | 0.0484 | 0.0473 | 0.0388 |
| GABA | 0.1132 | 0.3922 | 0.3240 | 0.3922 |
| Lys | 0.0219 | 0.0487 | 0.0459 | 0.0369 |
| His | 0.0304 | 0.0504 | 0.0486 | 0.0419 |
| Arg | 0.0243 | 0.0437 | 0.0387 | 0.0449 |
| Pro | 0.1901 | 0.2905 | 0.3163 | 0.6625 |
| total | 8.0641 | 13.5704 | 13.1792 | 12.7408 |

These results show that the amount of the total amino acids in the plant is remarkably increased by the introduction of maize Dof1 gene. Although the increase in the total amino acids was found irrespective of the kinds of the amino acids, the increase in glutamine, arginine and proline was remarkable when ammonia was supplied as a nitrogen source in the medium (corresponding the case of ½ MS medium). When the nitrogen source in the medium was only nitrates (in the case of PNS medium), the increase in the amino acid content was inclined to be less than that in the case of ½ MS medium but a considerable increase was observed, especially for glutamic acid and glutamine.

Example 7

NC Analysis of *Arabidopsis thaliana* Having Maize Dof1 Gene Introduced Thereinto Seeds of *Arabidopsis thaliana* containing maize Dof1 gene introduced thereinto and seeds of the control plant were planted on ½ MS medium containing the salts in an amount of ½ of those in Murashige and Skoog (MS) medium supplemented with or without 10 g/l sucrose. The seeds were cultivated under long-day conditions comprising 16 hours of light period and 8 hours of dark period at 22° C. for about 2 weeks to obtain the seedlings having about 5 or 6 true leaves. When the transformant was to be grown, 100 mg/l of kanamycin was added to the medium.

The quantitative determinations of nitrogen and carbon elements in these plants were conducted with Sumigraph NC-1000 (NC analyzer of Sumika Analysis Center).

The results are shown in Table 5.

TABLE 5

The results of NC analysis of transformed plants grown in 1/2 MS medium and 1/2 MS medium containing 10 g/l sucrose

|  | Columbia | | | Dof1-5 | | |
|---|---|---|---|---|---|---|
|  | N (mmole) | C (mmole) | N/C | N (mmole) | C (mmole) | N/C |
| 1/2 MS | 33.6 | 235.0 | 0.1429 | 42.1 | 275.0 | 0.1532 |
| 1/2 MS + Sucrose | 36.4 | 250.0 | 0.1457 | 42.9 | 294.2 | 0.1457 |

The numerals in Table 5 are given in terms of the mole of each element contained in 100 g fresh weight.

Those results indicate that the total nitrogen content of the plant body is remarkably increased by the introduction of maize Dof1 gene.

Example 8

Investigation of Growth of *Arabidopsis thaliana* Having Maize Dof1 Gene Introduced Thereinto in a Medium Containing Limited Nitrogen Seeds from *Arabidopsis thaliana* containing maize Dof1 gene introduced thereinto and seeds of the control plant were planted on ½ MS medium containing the salts in an amount of ½ of those in Murashige and Skoog (MS) medium in which the amount of nitrogen (30 mM) was reduced to ⅕ (6 mM) or ¹⁄₂₅ (1.2 mM). The seeds were cultivated under long-day conditions comprising 16 hours of light period and 8 hours of dark period at 22° C. for about 3 weeks. The fresh weight was determined.

The results are shown in Table 6

Table 6 Weight of fresh transformant grown in ½ MS medium (nitrogen concentration: 30 mM), in ½ MS medium having the nitrogen content reduced to ⅕ (nitrogen concentration: 6 mM) or in ½ MS medium having the nitrogen content reduced to ¹⁄₂₅ (nitrogen concentration: 1.2 mM)

|         | Nitrogen concentration | | |
|---------|-------|-------|--------|
|         | 30 mM | 6 mM  | 1.2 mM |
| Control | 1.00  | 0.99  | 0.51   |
| Dof1-5  | 1.00  | 1.03  | 0.80   |

The numerals in Table 6 are given in terms of the relative fresh weight of the plants grown in each medium to the average of fresh weight of the plants grown in ½ MS medium.

It was revealed that although the growth of the control plant was inhibited to about a half when nitrogen concentration was reduced to 1.2 mM, the degree of the inhibition of Dof1 transformed plant was about 20%, which indicated that the damage caused under the control of nitrogen was reduced. These results indicate that the plant can be tolerant to nitrogen deficiency by the introduction of maize Dof1 gene.

<Free Text of Sequence Listing>
SEQ ID NO: 1 and 2: PCR primer for maize Dof1
SEQ ID NO: 3 and 4: RT-PCR primer for maize Dof1
SEQ ID NO: 5 and 6: RT-PCR primer for beta-tubulin
SEQ ID NO: 7 to 10: RT-PCR primer for PEPC
SEQ ID NO: 11 to 14: RT-PCR primer for GLU1
SEQ ID NO: 15 and 16: RT-PCR primer for GS2

The present invention provides a transformed plant having an increased free amino acid content and/or a transformed plant having increased nitrogen content and/or a transformed plant tolerant to nitrogen deficiency and seeds of them. More specifically, according to the present invention, a transformed plant having the total free amino acid content increased to at least 1.5-fold, and seeds of them may be obtained. In particular, according to the present invention, a transformed plant is obtained where the free glutamine or glutamic acid content, the arginine content or the proline content is increased, and seeds of them may be obtained. Further, a transformed plant having the total nitrogen content increased to at least 1.2-fold, and seeds of them are obtained. In addition, a transformed plant may be obtained where the degree of the growth inhibition is reduced to 20% or below, and also seeds of them may be obtained.

What is claimed is:

1. A method for producing a transformed plant having a free amino acid content higher than that of naturally occurring plant of the same species cultivated under the same conditions and/or a plant having an increased nitrogen content and/or a plant tolerant to nitrogen deficiency, as compared with that of a naturally occurring plant of the same species cultivated under the same conditions, which comprises introducing a gene encoding maize Dof1 into a plant;

expressing the gene in the plant body; and selecting for plants having a free amino acid content higher than that of naturally occurring plant of the same species cultivated under the same conditions and/or a plant having an increased nitrogen content and/or a plant tolerant to nitrogen deficiency, wherein said transformed plant is selected from the group consisting of a member of the Cruciferae family, tomato, potato, wheat, rice plant, sugarcane, soybean, and sorghum.

2. The method according to claim 1, wherein the free amino acid is selected from the group consisting of asparagine, glutamine, glutamic acid and arginine.

3. The method according to claim 1, wherein the gene encoding mazie Dof1 is introduced into the plant and the obtained transformed plants are cultivated by supplying nitrogen in the form of ammonia as a nitrogen source.

4. The method according to claim 1, wherein the gene encoding mazie Dof1 is introduced into the plant and the obtained transformed plants are cultivated by supplying nitrogen only in the form of a nitrate as a nitrogen source.

* * * * *

SEQUENCE LISTING

```
<160> NUMBER OF SEQ ID NOS: 16

<210> SEQ ID NO 1
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
ttccattgcc cagctatctg tcactt                                    26

<210> SEQ ID NO 2
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
tcatcgcaag accggcaaca ggattc                                    26

<210> SEQ ID NO 3
<211> LENGTH: 23
<212> TYPE: DNA
```

```
<213> ORGANISM: ARTIFICIAL SEQUENCE
<220> FEATURE:
<223> OTHER INFORMATION: SYNTHETIC DNA

<400> SEQUENCE: 3
cccagcgccg tcgcgcatgc agg                                              23

<210> SEQ ID NO 4
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
tgaccgtgtg tggctgtcac ggg                                              23

<210> SEQ ID NO 5
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
ctcgtggatc acagcaatac agagcc                                           26

<210> SEQ ID NO 6
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
tcctcctgca cttccacttc gtcttc                                           26

<210> SEQ ID NO 7
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ggtttcggag cagcatttag gtatgc                                           26

<210> SEQ ID NO 8
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
ttaaccggtg ttttgcaatc ctgcag                                           26

<210> SEQ ID NO 9
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
aaccaatggc cattcaaccg tgtcac                                           26
```

<210> SEQ ID NO 10
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
ttaaccggtg ttttgcatac cagcag                                26

<210> SEQ ID NO 11
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
atgatgcagc gagtattcac ctttgg                                26

<210> SEQ ID NO 12
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
agcgagggaa gctccaatgt cacgtt                                26

<210> SEQ ID NO 13
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
atgactggtg gctgtgtagt cgtgct                                26

<210> SEQ ID NO 14
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
caactgccac aacctgctct tgaatg                                26

<210> SEQ ID NO 15
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
atggctcaga tcttagcagc ttctcc                                26

<210> SEQ ID NO 16
<211> LENGTH: 26
<212> TYPE: DNA
<213> ORGANISM: ARTIFICIAL SEQUENCE
<220> FEATURE:

```
-continued

<223> OTHER INFORMATION: SYNTHETIC DNA

<400> SEQUENCE: 16
atcacttcac tatcttcacc aggtgc                                        26
```